(12) United States Patent
Su

(10) Patent No.: US 10,925,794 B2
(45) Date of Patent: Feb. 23, 2021

(54) STATIONARY MASSAGE DEVICE, SYSTEM AND METHODS FOR SOFT TISSUE STRAIN RELEASE

(71) Applicant: Jason T. Su, Cupertino, CA (US)

(72) Inventor: Jason T. Su, Cupertino, CA (US)

( * ) Notice: Subject to any disclaimer, the term of this patent is extended or adjusted under 35 U.S.C. 154(b) by 0 days.

(21) Appl. No.: 15/658,413

(22) Filed: Jul. 25, 2017

(65) Prior Publication Data
US 2019/0029908 A1 Jan. 31, 2019

(51) Int. Cl.
*A61H 1/00* (2006.01)
*A61H 1/02* (2006.01)
(Continued)

(52) U.S. Cl.
CPC .............. *A61H 1/02* (2013.01); *A61F 7/007* (2013.01); *A61F 7/0097* (2013.01); *A61F 7/02* (2013.01); *A61F 7/03* (2013.01); *A61F 7/08* (2013.01); *A61H 1/006* (2013.01); *A61H 7/00* (2013.01); *A61H 7/001* (2013.01); *A61H 7/002* (2013.01); *A61H 7/003* (2013.01); *A61F 2007/0052* (2013.01); *A61F 2007/0207* (2013.01); *A61F 2007/0223* (2013.01); *A61F 2007/0228* (2013.01); *A61F 2007/0231* (2013.01); *A61F 2007/0233* (2013.01);
(Continued)

(58) Field of Classification Search
CPC .......... A61H 1/02; A61H 7/002; A61H 1/006; A61H 7/00; A61H 7/001; A61H 7/003; A61H 2201/0126; A61H 2201/0138; A61H 2201/0149; A61H 2201/0207; A61H 2201/0214; A61H 2201/0228; A61H 2201/0278; A61H 2201/0292; A61H 2201/1619; A61H 2201/1623; A61H 2201/165; A61H 2201/1671; A61H 2201/169; A61H 2201/1692; A61F 2007/0052; A61F 2007/0207; A61F 2007/0223; A61F 2007/0228; A61F 2007/0231; A61F 2007/0233; A61F 2007/0242
See application file for complete search history.

(56) References Cited

U.S. PATENT DOCUMENTS

| | | | | |
|---|---|---|---|---|
| 2,972,833 | A * | 2/1961 | La Grutta | A63H 33/062 446/110 |
| 3,034,254 | A * | 5/1962 | Christiansen | A63H 33/086 446/128 |

(Continued)

*Primary Examiner* — Steven O Douglas

(57) ABSTRACT

A stationary massage device, system and corresponding methods are used for self-administered or assisted soft tissue strain release (including trigger point therapy, strain-and-counterstrain therapy and neuromuscular release). The massage device comprises a body, wherein the body may include branches, each having flat surfaces, edges, ridges or corners. The surfaces, edges and ridges may be pushed along the myofilament direction of the soft tissues to produce pressing, rubbing, stretching and pulling actions on the soft tissues as stripping massages. The system can be configured to form different geometric shapes, and made of different materials of different firmness. The system can be further configured to perform unheated, or heated massages; and cooling treatments. In addition to being used alone, the system can be mounted on a piece of wall, a standing frame, furniture or a garment.

3 Claims, 18 Drawing Sheets

(51) Int. Cl.
*A61H 7/00* (2006.01)
*A61F 7/00* (2006.01)
*A61F 7/03* (2006.01)
*A61F 7/08* (2006.01)
*A61F 7/02* (2006.01)

(52) U.S. Cl.
CPC ............... *A61F 2007/0242* (2013.01); *A61H 2201/0126* (2013.01); *A61H 2201/0138* (2013.01); *A61H 2201/0149* (2013.01); *A61H 2201/0207* (2013.01); *A61H 2201/0214* (2013.01); *A61H 2201/0228* (2013.01); *A61H 2201/0278* (2013.01); *A61H 2201/0292* (2013.01); *A61H 2201/165* (2013.01); *A61H 2201/169* (2013.01); *A61H 2201/1619* (2013.01); *A61H 2201/1623* (2013.01); *A61H 2201/1671* (2013.01); *A61H 2201/1692* (2013.01)

(56) References Cited

U.S. PATENT DOCUMENTS

| | | | | |
|---|---|---|---|---|
| 3,084,975 A * | 4/1963 | Winrow | ............... | A47C 17/045 297/119 |
| 3,103,219 A * | 9/1963 | Chadner | ............... | A61F 7/007 219/217 |
| 4,483,328 A * | 11/1984 | Wolocko | ............... | A61H 1/008 601/135 |
| 5,350,256 A * | 9/1994 | Hammer | ............... | E02D 29/025 405/262 |
| 5,389,063 A * | 2/1995 | Wu | ............... | A61H 7/001 273/153 S |
| D374,484 S * | 10/1996 | Haynes | ............... | D24/214 |
| 5,882,082 A * | 3/1999 | Moore | ............... | A47C 16/025 297/423.44 |
| 6,124,578 A * | 9/2000 | Elliot | ............... | A47G 9/1036 219/217 |
| 6,256,818 B1 * | 7/2001 | Hughes | ............... | A47G 9/1036 5/421 |
| 6,269,654 B1 * | 8/2001 | Murray | ............... | B32B 3/04 62/457.1 |
| 6,299,585 B1 * | 10/2001 | Yoo | ............... | A61H 7/001 601/118 |
| 6,933,478 B2 * | 8/2005 | Lewis | ............... | A61F 7/007 219/211 |
| 2004/0243035 A1 * | 12/2004 | Devlin | ............... | A61H 15/0092 601/131 |
| 2005/0049526 A1 * | 3/2005 | Baer | ............... | A61H 7/003 601/15 |
| 2008/0208298 A1 * | 8/2008 | Mizrahi | ............... | A61F 7/02 607/108 |
| 2012/0253248 A1 * | 10/2012 | Carlson | ............... | A61H 15/00 601/128 |

* cited by examiner

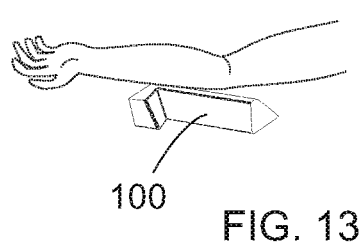
100  FIG. 13
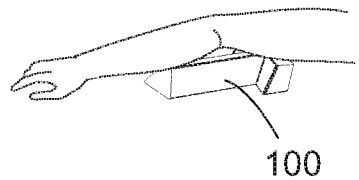
100  FIG. 14
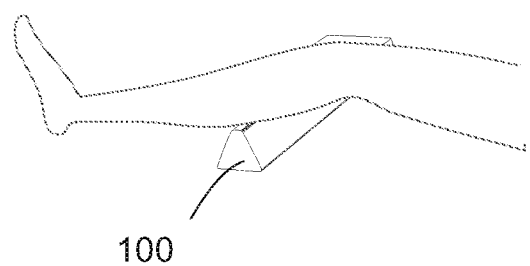
FIG. 15
100
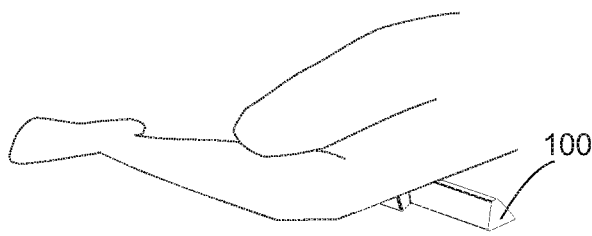
FIG. 16
100
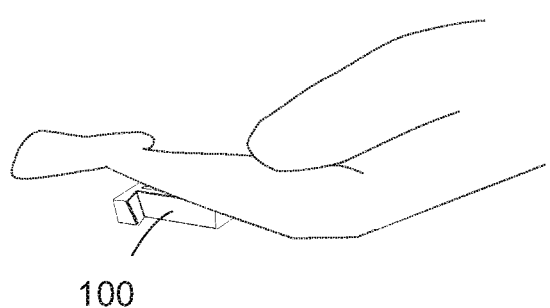
FIG. 17
100
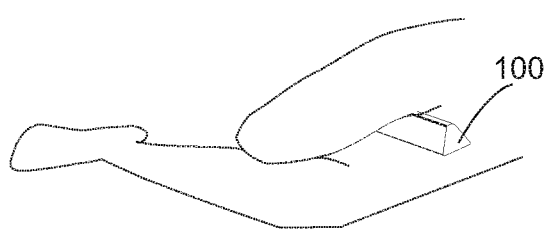
100  FIG. 18

STATIONARY MASSAGE DEVICE, SYSTEM AND METHODS FOR SOFT TISSUE STRAIN RELEASE

REFERENCES CITED

| | | |
|---|---|---|
| 5,643,182 | Jul. 1, 1997 | James E. Engel |
| 8,932,322 | Jan. 13, 2015 | Jonathan F. Reynolds, et al. |
| 2,013,0085426 | Apr. 4, 2013 | Marc Brodsky |
| 6,866,776 | 15/15/2005 | Wendy Zeller Leason, et al. |
| 5,024,215 | Jun. 18, 1991 | Jason Wang |
| 6,911,010 B2 | Jun. 28, 2006 | Dirks et al. |
| 4,604,993 | Aug. 12, 1986 | Moriwaki et al. |

FIELD OF THE INVENTION

The present invention relates to soft tissue strain release (including trigger point therapy, strain-and-counterstrain therapy and neuromuscular release) therapy devices, systems and methods. More particularly, the present invention relates to soft tissue strain release therapy which emphasizes stripping and passive stretching.

BACKGROUND

Soft tissue strain release (including trigger point, strain-and-counterstrain and neuromuscular release) therapy is a method commonly used by physical and massage therapists, osteopaths and chiropractors to treat soft tissue relate pains, and to restore physical healthiness and functions of a patient. A properly design soft tissue strain release device or system can facilitate the practice of these health care professional, and reduce the risk of their work injuries. It can also enable the patients to perform self-administrated therapies away from a clinic, and increase the frequency of the intervention as they are often time required.

Conventionally available devices for this application herein described are canes, balls, rollers and hand-held or mounted probes. They generally make contact with the body in two shapes: ball or cylinder. The rolling or probing action mainly generates forces perpendicular to the skin surface, which are called normal forces. They generate relatively low amount of forces lateral to the skin surface, which are called shear forces, compared to stripping massage as a massage therapist does with his or her hands. Therefore, the conventional massage devices don't achieve the full effectiveness of the hand massage that involves stripping actions. A massage device such as in U.S. Pat. No. 5,643,182 demonstrates a cylinder-shaped massager that rolls on the skin. Massage devices such as in U.S. Pat. No. 8,932,322 and US20130085426 demonstrate ball-shaped massagers that probe at trigger points.

In order to generate sufficient shear forces to achieve the full effectiveness of a massage therapy, the massage device must possess the following capabilities: 1) sitting still against the movement of the user's body, 2) distributes the forces in strip shape (long and narrow), moving in parallel (0 degree) along or at a small angle to the direction of the myofilaments.

Ideally, this massage device should still have pointy parts available to probe trigger points alone. It should be able to fit various locations of the body, too, stripping and probing alike. It should further address the needs of a massage with heating and cooling treatments.

SUMMARY OF THE INVENTION

Disclosed herein is the present invention "Stationary Massage Device, System and Methods for Soft Tissue Strain Release". The object of the present invention is to provide an apparatus, a system, and methods that can facilitate self-administrated as well as assisted stripping and probing massage therapies.

It is yet another objective of the invention to provide a massage device, a system, and methods which temperature can be raised or lowered to meet the requirements of certain treatments.

In one embodiment, the soft tissue strain release system comprises a tool. The tool comprises a bar-shaped body, wherein the body includes multiple surfaces. The surfaces form edges, ridges or corners: the edges defined by the joint of two surfaces; the ridges defined by a strip of flat narrower surface rising above some of other surfaces, or sitting on the top of some of its surrounding surfaces when the body lies at certain positions; and the corners defined by pointy parts that may be formed by the joint of three or more surfaces.

In another embodiment, the soft tissue strain release system comprises a tool. The tool comprises a body, wherein the body includes one or multiple sections connected together, each section constituting an embodiment of the hereinbefore mentioned embodiment.

In yet another embodiment, the soft tissue strain release system comprises a tool. The tool comprises a body, wherein the body includes one or multiple of the embodiments mentioned hereinbefore, and a heating source surrounding around or embedded inside the body.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Advantageous Effects of the Invention

The present invention "Stationary Massage Device, System and Methods for Soft Tissue Strain Release" has the following main advantageous effects: 1) having a flat and branched surface to form a stable bottom, and allowing the massage system to have a good grip on the surface where the massage system sits, producing the stability for shear force generation a stripping massage requires; 2) having the flexibility of doing any combination of stripping and probing massages through the combination of the edges and corners made in different orientations in one single system; 3) simply by rotating the system and aligning it at different angles with respect to his or her body, the user being able to press two trigger points separated by various distances; 4) having different geometric shapes formed by different ends of different sections permitting the users to fit said system in different locations of their bodies; 4) each branch or section of the system serving any of the following purposes: a contact component, a handle and an anchor.

BRIEF DESCRIPTION OF THE DRAWINGS

FIG. 13-34 are illustrations of the use of a stationary message device for soft tissue strain release according to certain embodiments.

DETAILED DESCRIPTION

In the following descriptions, the present invention will be explained with reference to example embodiments thereof. However, these example embodiments are not intended to limit the present invention to any specific example, embodiment, environment, applications or particular implementations described in these example embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

Figure 1:
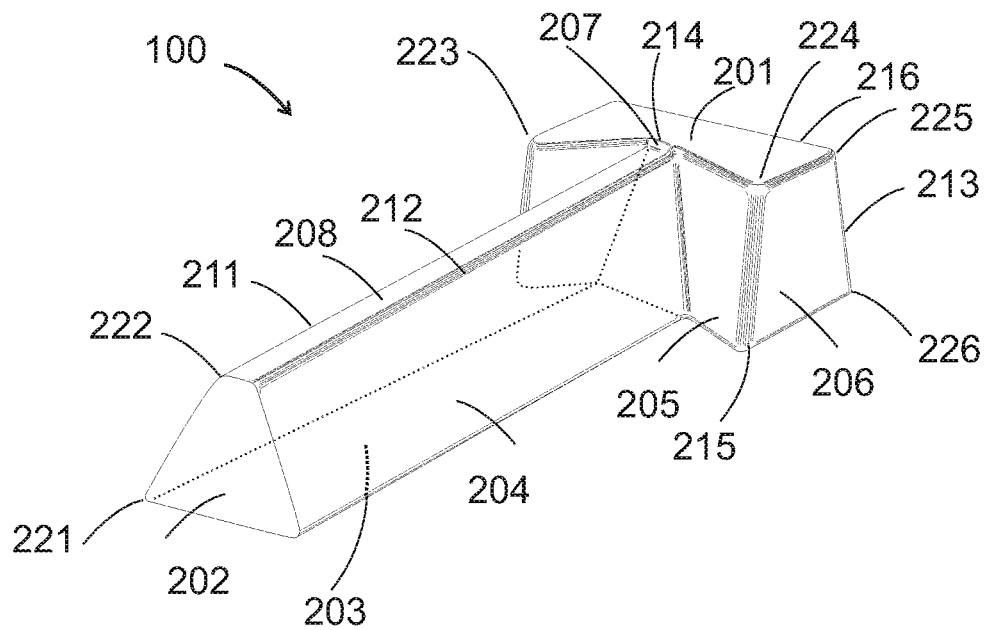
FIG. 1 is a perspective view of a stationary message device for soft tissue strain release according to certain embodiments.

Referring first to FIG. 1-10, various embodiments of the present invention of stationary massage device for soft tissue strain release are shown. Referring to FIG. 1, the device comprises a body 100 including multiple surfaces 201-208, edges 211-216, and corners 221-226. The surfaces 201-208 can be of any shape, preferably a polygon such as a trapezoid, a rectangle, a triangle or a square. The edges 211-216 formed at the junction of two of the surfaces 201-208, can have curvatures of any radius, small radius for deeper stripping massage actions, and large radius for more superficial rubbing actions. The corners 221-226 are formed where 3 or more of the surfaces 201-208 join together. The corners 221-226 may have curvatures of any radius. These examples of the embodiments of the present invention are provided to facilitate the description and understanding, but not to limit the choices of implementation.

Figure 2:
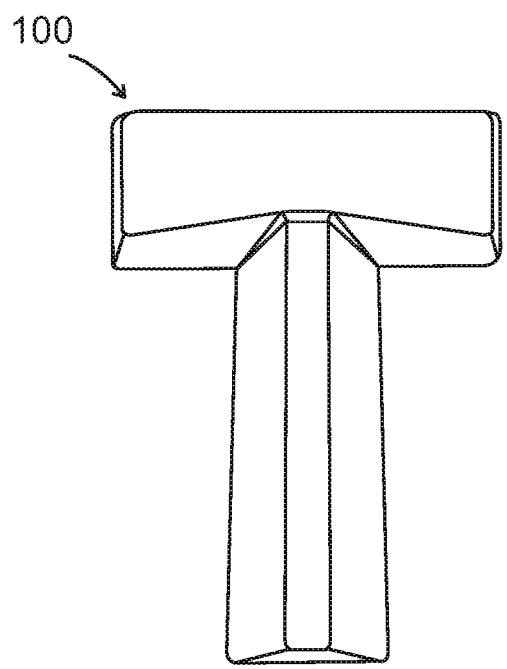
FIG. 2 is a top view of a stationary message device for soft tissue strain release according to certain embodiments.
Figure 3:
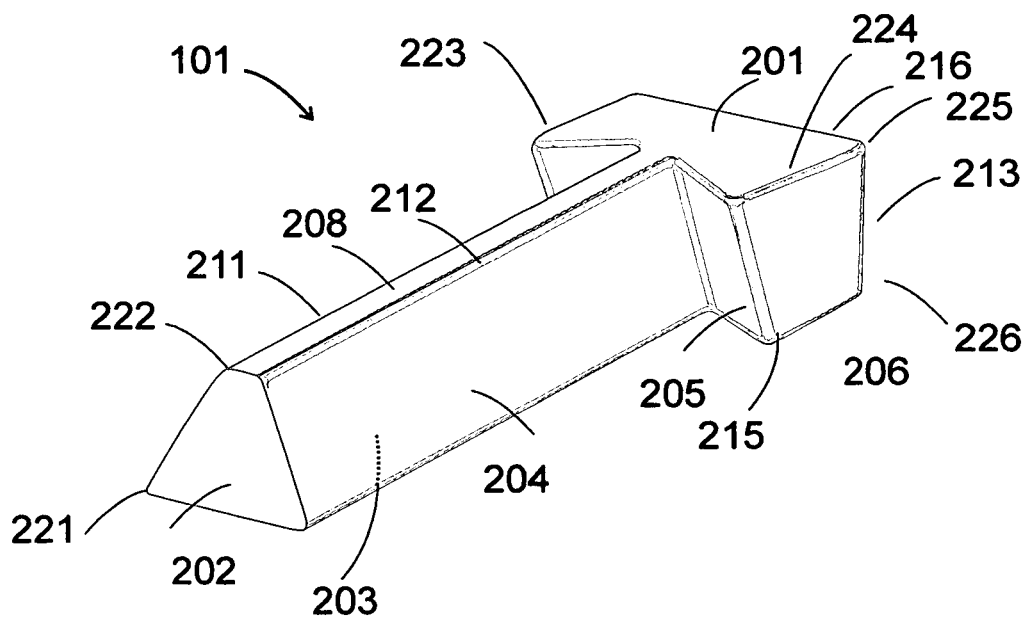
FIG. 3 is a perspective view of a stationary message device for soft tissue strain release according to certain embodiments.
Figure 4:
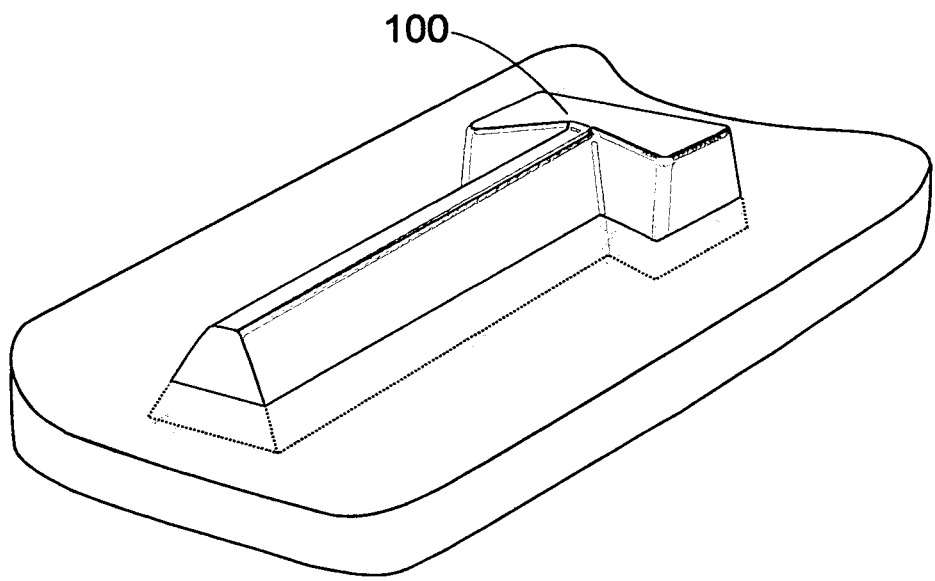
FIG. 4 is a perspective view of a stationary message device for soft tissue strain release according to certain embodiments.

Referring to FIG. 1-4, two bodies 100 and 101 with different proportions of the top surfaces 208 and the bottom surfaces 203 are illustrated. As demonstrated, the surfaces 201-208 and edges 211-216 can be made of different proportions without departing from the scope of the invention. The body of the massage device may comprise a single section or multiple sections connected to each other. Each of the sections thereof can be made straight or curved. As illustrated in FIG. 1-2, the body of the device includes three connected sections that form together a T-shaped cross section on its horizontal planes.

Figure 5:
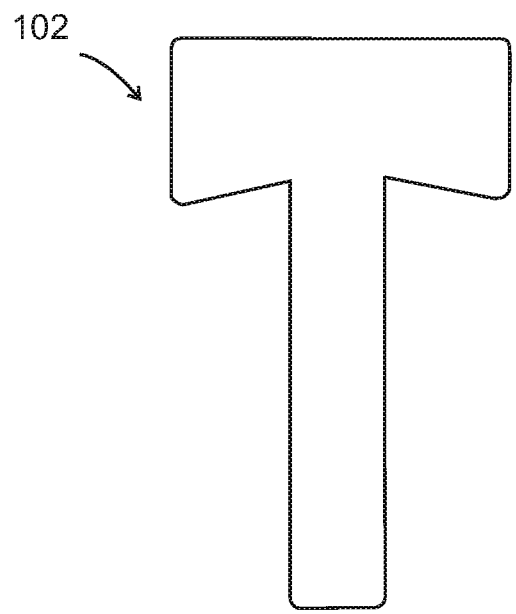
FIG. 5 is a horizontal cross section view of a stationary message device for soft tissue strain release according to certain embodiments.
Figure 6:
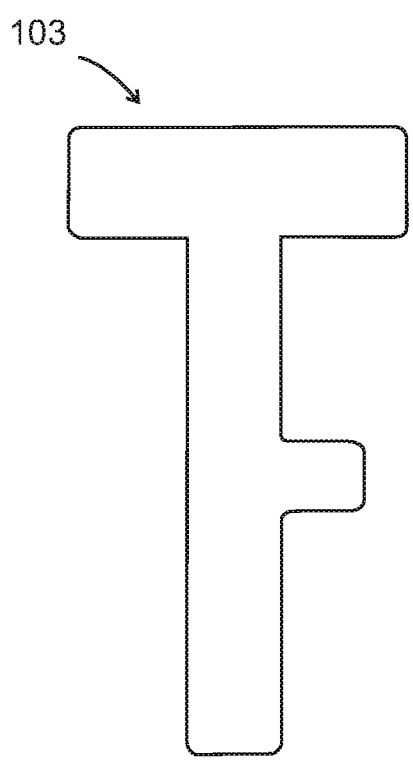
FIG. 6 is a horizontal cross section view of a stationary message device for soft tissue strain release according to certain embodiments.

FIGS. 5 and 6 illustrate embodiments having different top views, one having T shape, and the other F shape. Comprising different counts and shapes of said sections allows the user to reach different locations of his or her body.

Figure 7:
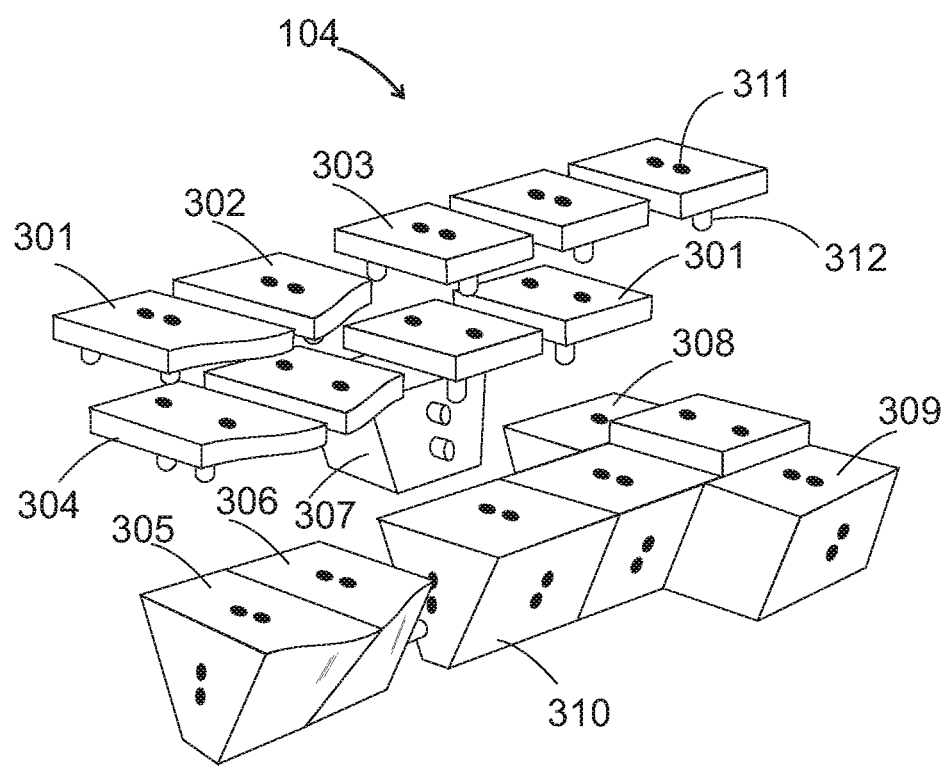
FIG. 7 is a perspective view of a stationary message device for soft tissue strain release according to certain embodiments.

Referring to FIG. 7, an embodiment of the present invention comprises body 104 that has a plurality of smaller components 301-310, each having pegs 311 and holes 312 to hold each other together when assembled. Components 301-310 can be arranged in any style to scale up or down the dimensions of any surface, and any edge of body 104. The sizes, the shapes and the numbers of components 301-310, and of their pegs 311 and holes 312 can be varied without departing from the scope of the invention. The methods of bonding components 301-310 is not limited to pegs 311 and holes 312 as exemplified in FIG. 7. There are presented to facilitate the illustration of the present invention, and can be replaced with other methods such as screws, Velcro or glue without departing from the scope of the invention.

Figure 8:
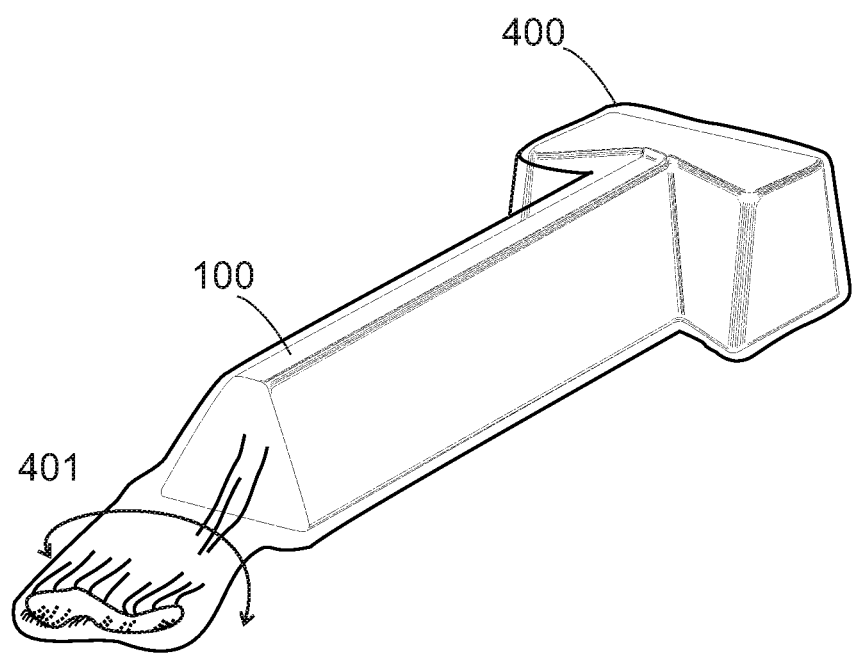
FIG. 8 is a perspective view of a stationary message device for soft tissue strain release according to certain embodiments.

The bodies 100-104 shown in FIG. 1-7 can be made of any type of natural or manmade materials, such as wood, glass, metal, plastic, rubber, and ceramic, or of a combination of two or more of them. Referring to FIG. 8, an embodiment 105 of the present invention comprising two different materials is shown. Body 105 includes body 100 made of a hard material, and wrapper 400 made of soft fabric. Wrapper 400 permits the user to change the firmness and the texture of the contacts, and, in turn, the depth of the pressing and the friction of rubbing, respectively. A tail 401 of wrapper 400 may be made as an extension to facilitate the handling and the anchoring during application.

Figure 9:
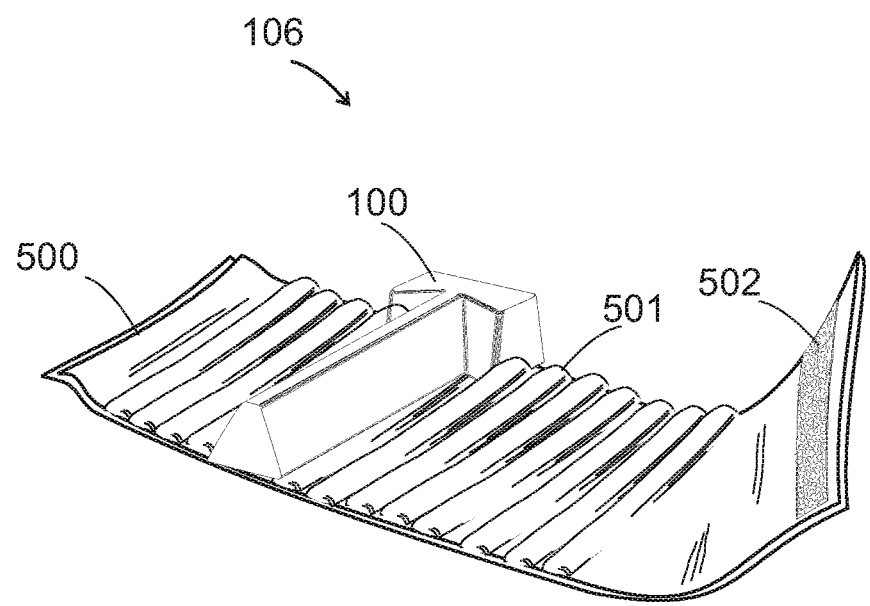
FIG. 9 is a perspective view of a stationary message device for soft tissue strain release according to certain embodiments.
Figure 10:
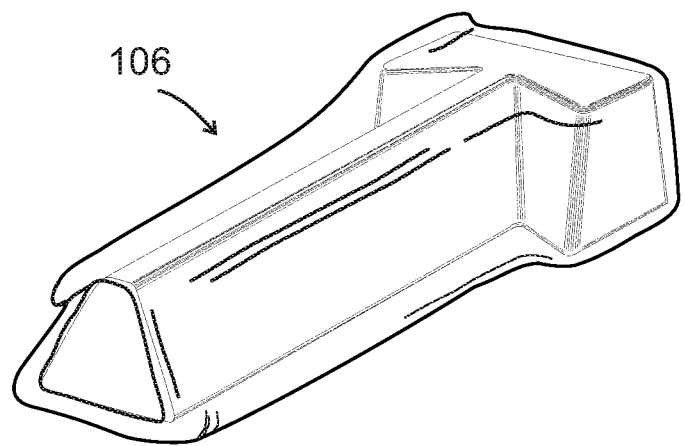
FIG. 10 is a perspective view of a stationary message device for soft tissue strain release according to certain embodiments.

Referring to FIGS. 9 and 10, wrapper 500 for heated massage is illustrated. In this embodiment, body 100 is wrapped by a heating wrapper 500. Heating wrapper 500 comprises pockets 501 that contain rice grains, beans or any material with practically high heat capacity that can be heated up by microwave, thereafter, hold the heat, and gradually release the heat over a reasonably long period of time. The wrapper 500 may include, but not limited to, a securing method Velcro tape 502.

Figure 11:
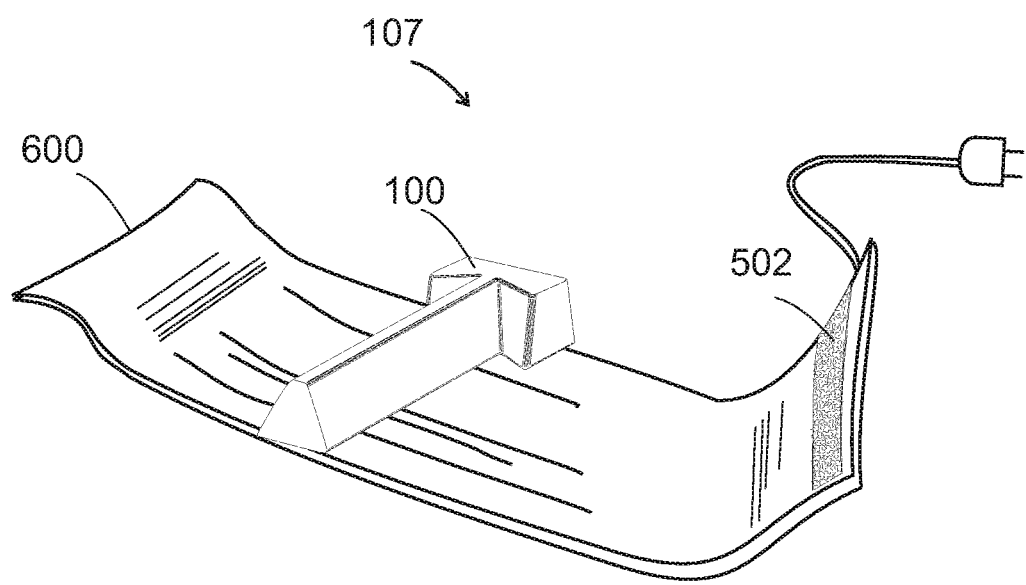
FIG. 11 is a perspective view of a stationary message device for soft tissue strain release according to certain embodiments.
Figure 12:
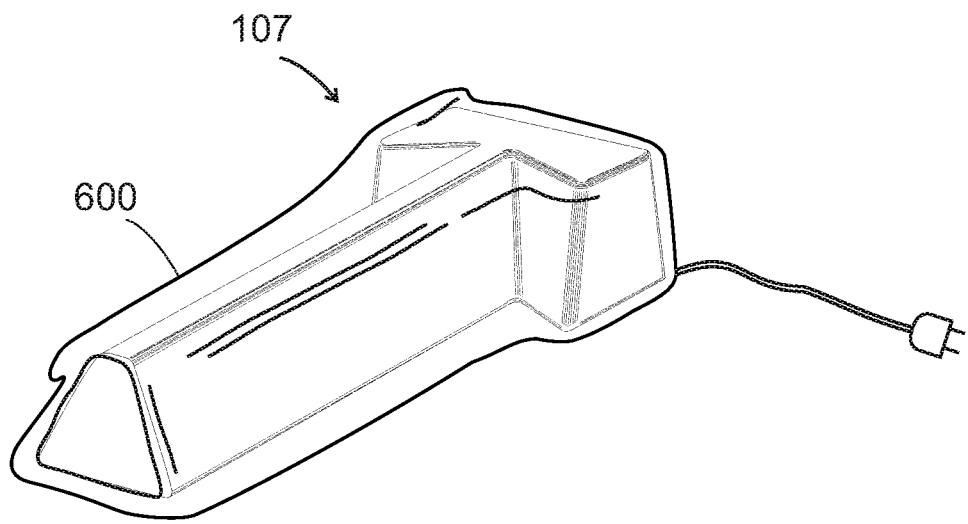
FIG. 12 is a perspective view of a stationary message device for soft tissue strain release according to certain embodiments.
Figure 19:
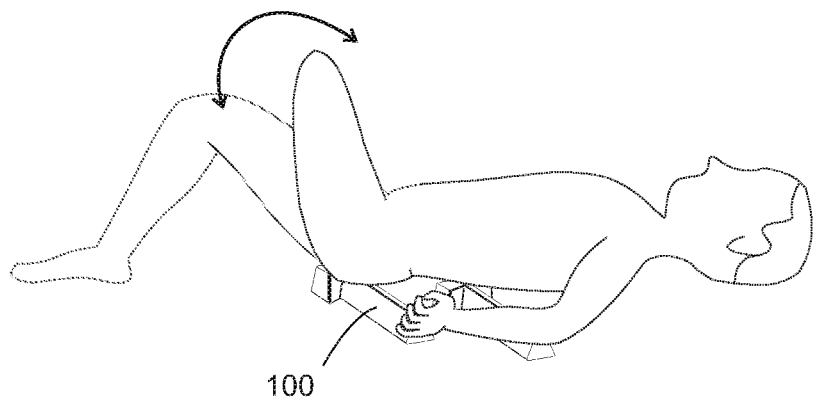
Figure 20:
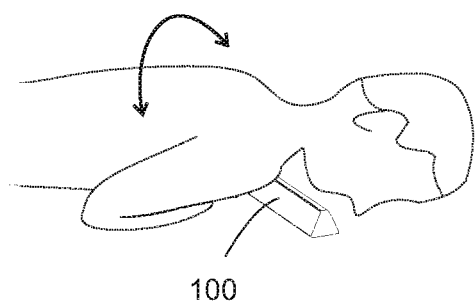
Figure 21:
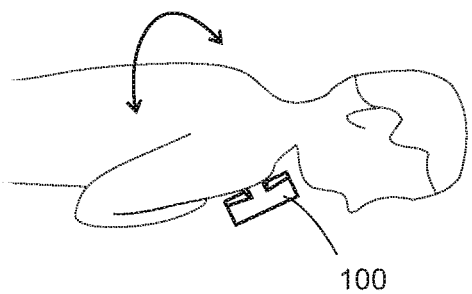
Figure 22:
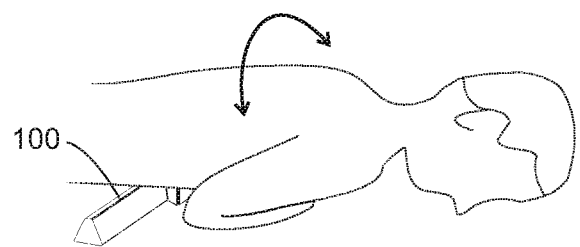
Figure 23:
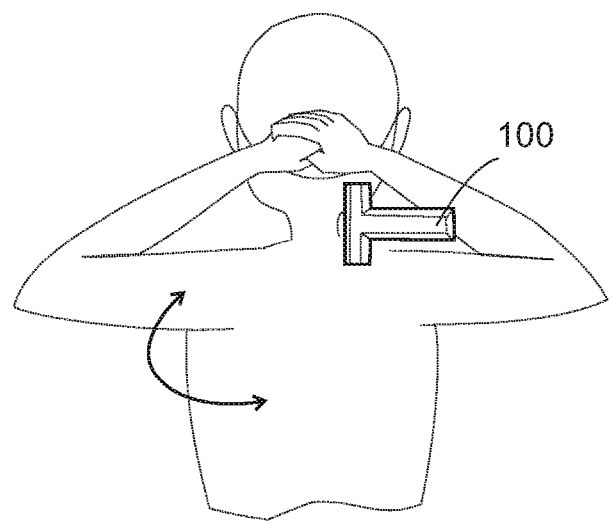
Figure 24:
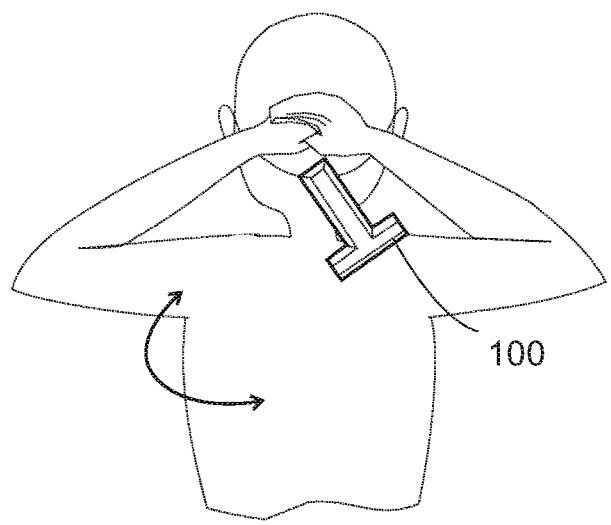

Referring to FIGS. 11 and 12, another heating method is illustrated. In this embodiment, body 100 is wrapped by electrically heated blanket wrapper 600.

FIG. 13-34 demonstrate the use of one of the embodiments of the present invention of stationary massage devices for soft tissue strain release. Referring to FIG. 17-24, the user identifies the zones needed to be treated, lying face up if the zones are found on the back side, or lying face down if the zones are on the frontal side. The user thereafter puts device 100 under his or her body, and presses the soft tissues against the edges and/or corners of device 100 with his or her body weight and movement. Stationary massage device 100 sits still, stretching, rubbing or probing the soft tissues as the user moves his or her body. With some adjustment on the location and the angle of device 100 after it is placed, the user finds the optimal position to perform the massage. Simultaneous stripping, rubbing and probing at various locations in proximity are performed that yields the effects most similar to massages by the hands of a physical therapist or a masseuse. This is what a conventional cylinder-shaped roller, or a spherical or pointy probe massage device cannot do.

Figure 25:
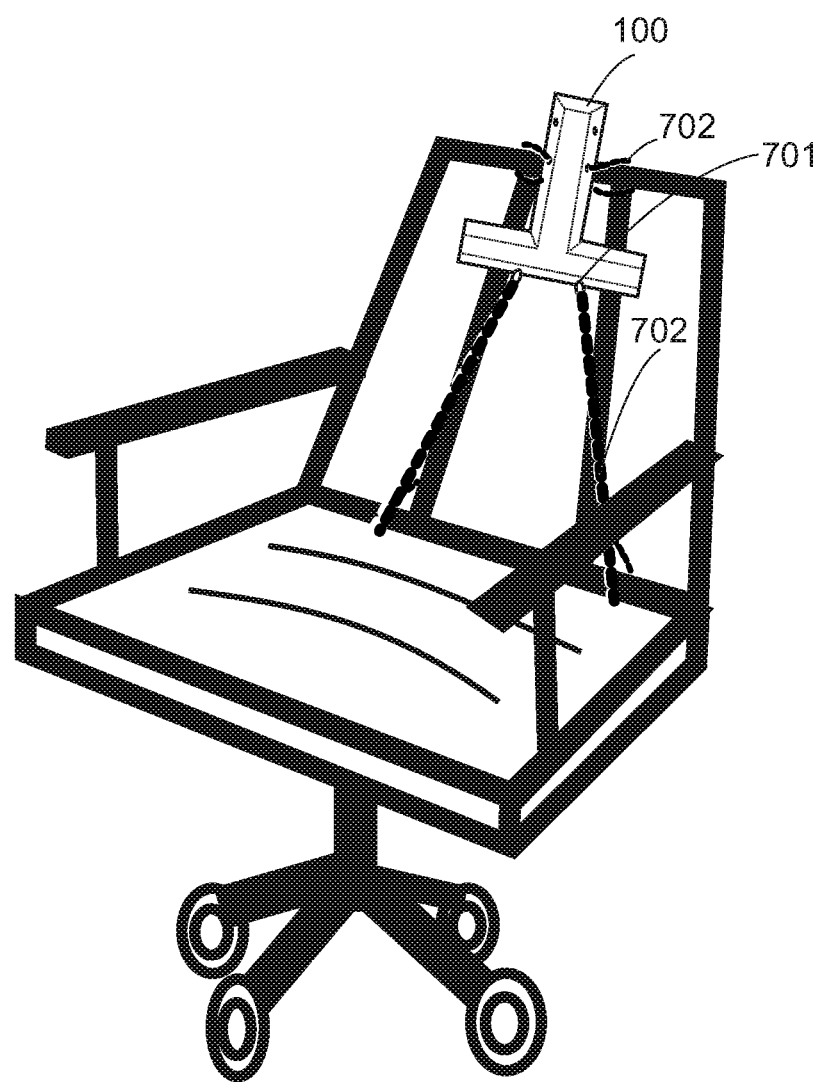

Referring to FIG. 25, an embodiment of stationary massage device 100 including components hooks 701 and strings is 702 is illustrated. The securing components such as 701 and 702 enable the device to be mounted on furniture. In this example, device 100 is mounted on a chair. This system can be very useful in reducing the risk of repetitive stress (strain) injury at a work place when it is made commonly available, and its self-administered massage as a common practice is promoted.

Figure 26:
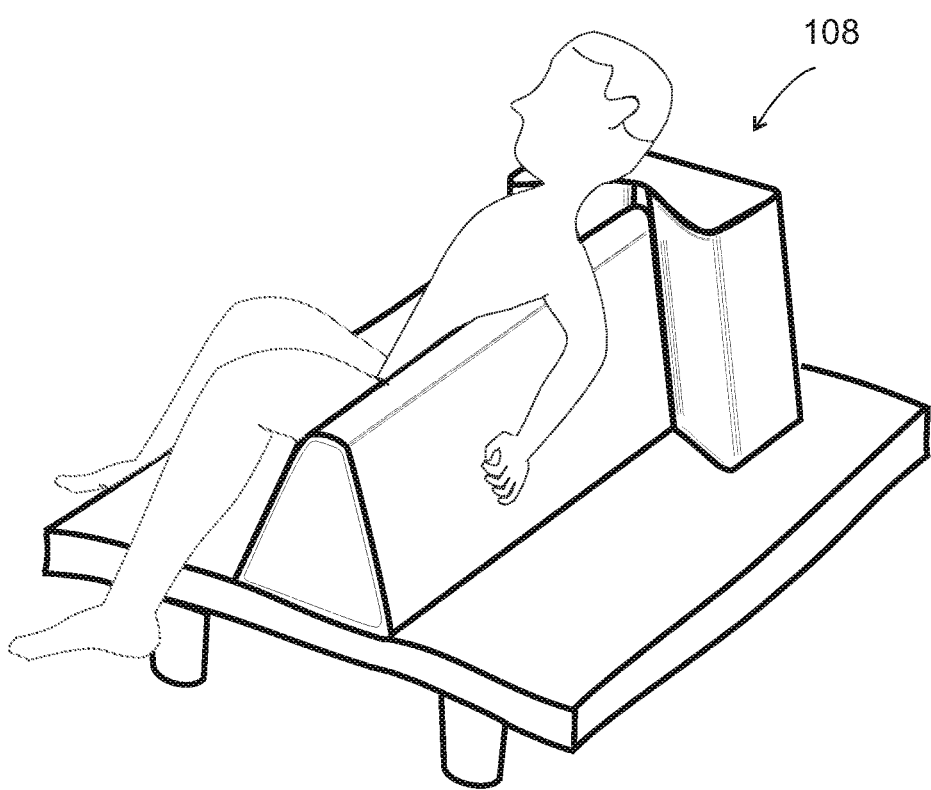
Figure 27:
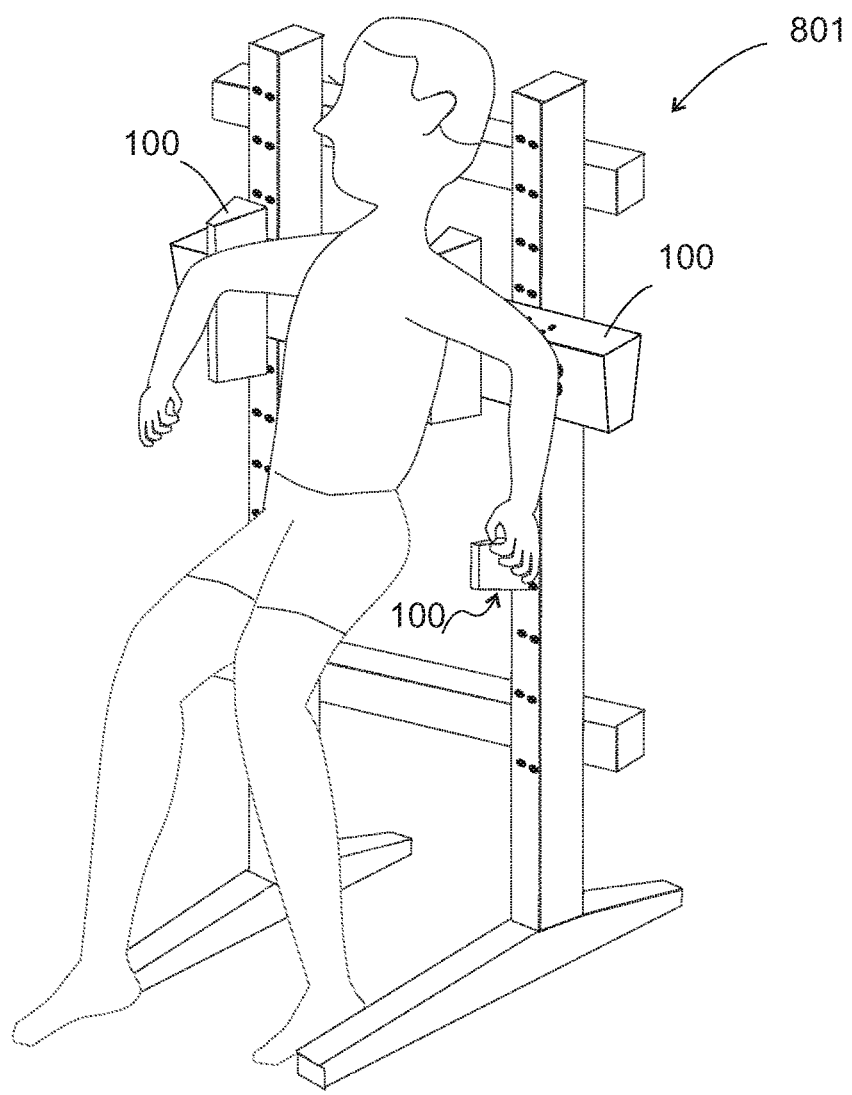
Figure 28:
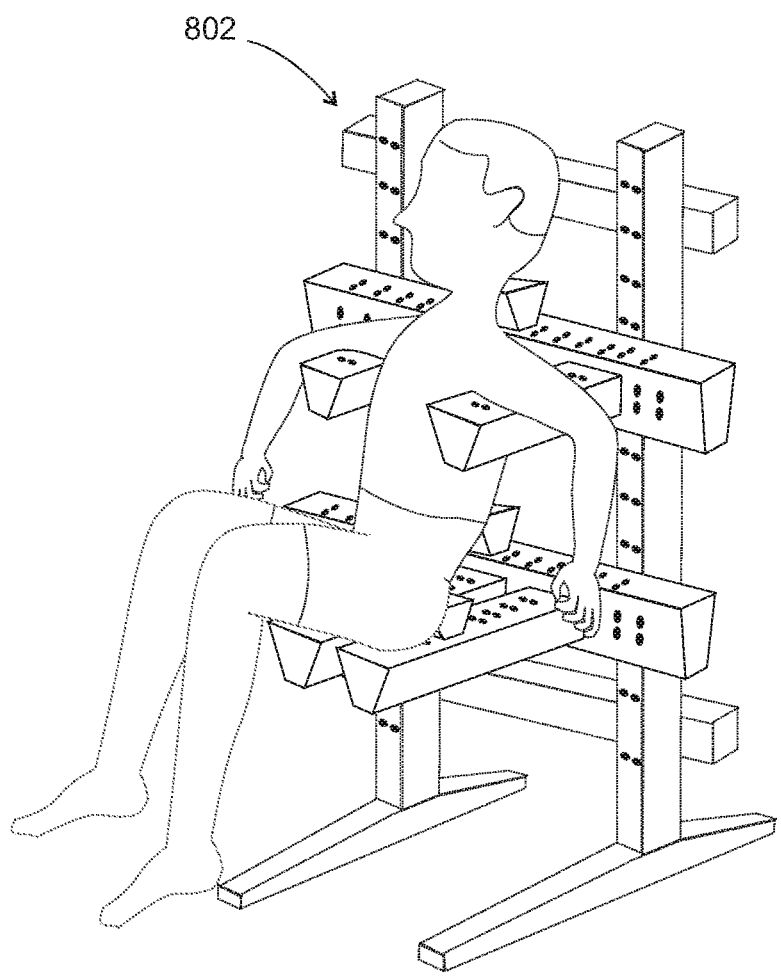
Figure 29:
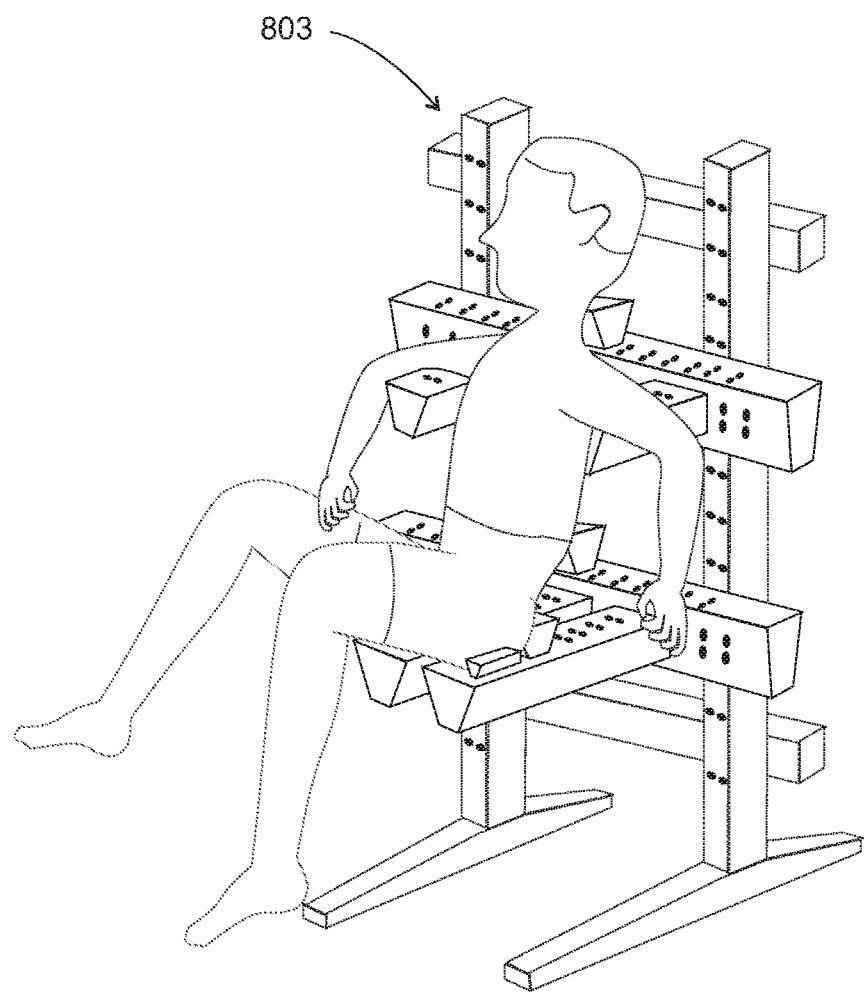
Figure 30:
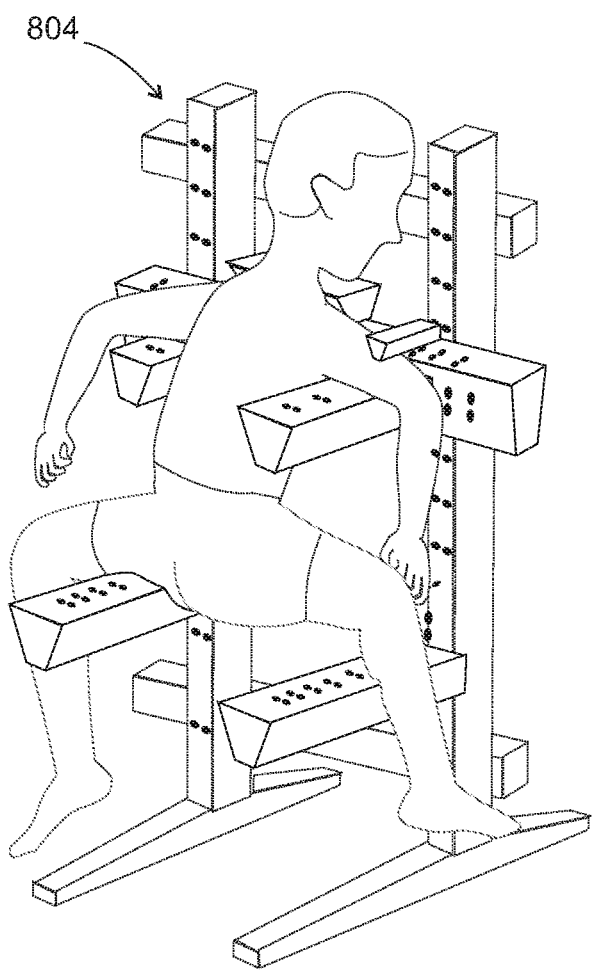
Figure 31:
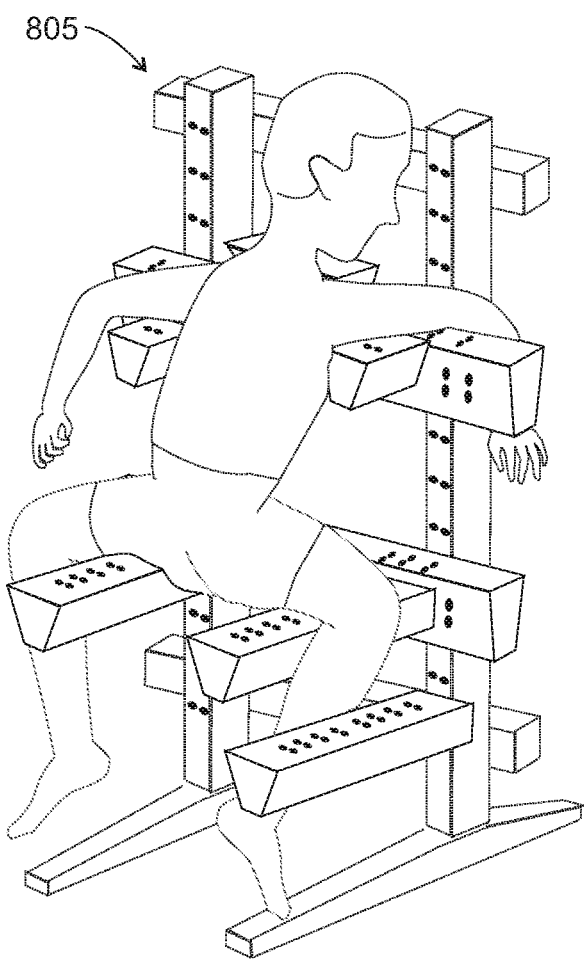

Referring to FIG. 26, an embodiment of stationary massage device 108 is shaped and sized in such a way that the user may recline in it as a chair or a couch. Having his or her strained soft tissues in the back or in the shoulder areas, the user may sit with his or her back pressed and moved against one of the edges of device 108. Similarly, the user may lie facing downward with his or her chest leaning toward the device to treat the strained soft tissues in the chest or in abdominal areas. System including device 108 or a furniture comprising device 108 is very useful at a rehabilitation center, a nursing home, or even a work place where regular soft-tissue-strain-releasing exercise is a key component of maintaining or restoring the healthiness of its member.

Referring to FIG. 27-31, a single or multiple stationary massage devices 100 are mounted on a standing mounting frame 801-805. They provide further stability and flexibility. The mounting positions of stationary massage devices 100 can be configured differently as shown. The flexibility permits the user to access certain hard-to-reach areas that can be only exposed when the user is sitting or reclining in some unique positions the standing frame enables him or her to take. However, the systems with mounting frames 801-804 required more space, and aren't as easy to carry around as a portable counterpart. Therefore, they are suitable for clinic applications where many users may visit and share the equipment. They are also very suitable for fitness centers, sports clubs, pharmacy, shopping centers or places like these where a larger space and public access are available, and the exercises of early prevention of the sports-related injuries are beneficial.

Figure 32:
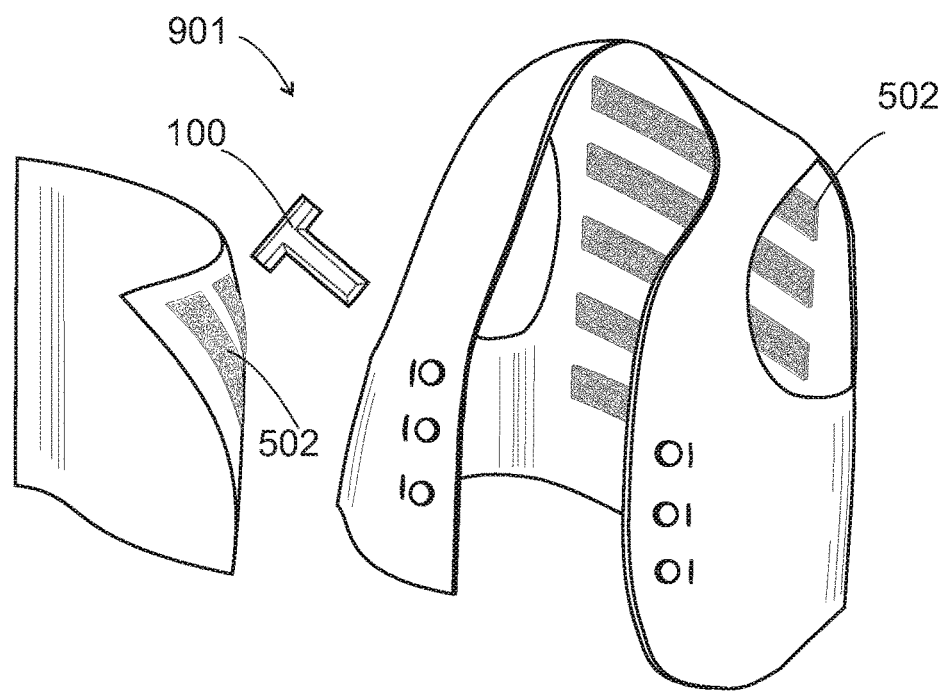
Figure 33:
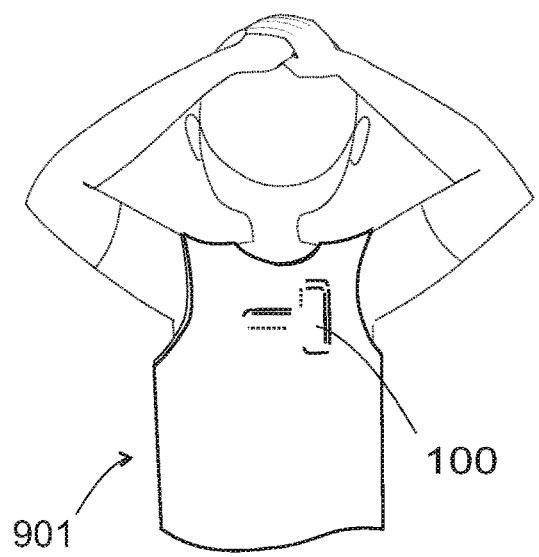
Figure 34:
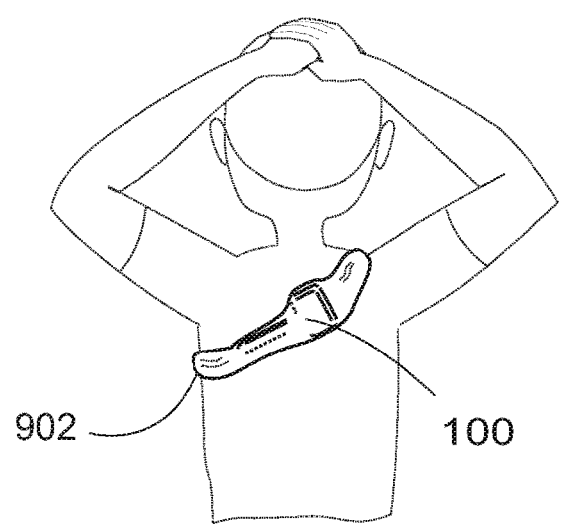

Referring to FIG. 32-33, an embodiment with Velcro garment 901 comprising massage system 100 is shown. Referring to FIG. 34, similarly, an embodiment with strap or belt massage wear 902 comprising system 100 is shown. They provide further flexibilities of the use of the current invention.

The above disclosure is related to the detailed technical contents and inventive features thereof. People skilled in this field may proceed with a variety of modifications and replacements based on the disclosures and suggestions of the invention as described without departing from the characteristics thereof. Although such modifications and replacements may not be fully disclosed in the above descriptions, the following claims will further cover possible variations within the scope of the invention.

What is claimed is:

1. A massage system comprising:
   a first portion extending along a first direction; and
   a second portion extending along a second direction perpendicular to the first direction;
   wherein the first portion is directly attached to the second portion; and
   wherein the first portion and the second portion form a letter T shape;
   wherein the first portion comprises a top surface;
   wherein the second portion comprises a top surface; and an inclined surface;
   wherein the inclined surface of the second portion connects the top surface of the second portion to the top surface of the first portion; and
   wherein the top surface of the second portion is located at a position lower than the top surface of the first portion.

2. The massage system of claim 1 further comprising a wrapper wrapping around the first portion and the second portion;
   wherein the wrapper comprises a tail facilitating handling and anchoring of the massage system;
   wherein the first portion and the second portion are made of a first material; and
   wherein the wrapper is made of a second material; and
   wherein the first material is harder than the second material.

3. The massage system of claim 1, wherein the first portion comprises
   a first plurality of hooks; a first plurality of strings attached to the first plurality of hooks;
   wherein the second portion comprises a second plurality of hooks; and a second plurality of strings attached to the second plurality of hooks; and
   wherein the massage system is configured to be mounted on a chair by the first plurality of strings and the second plurality of strings.

* * * * *